United States Patent [19]

Oliva et al.

[11] Patent Number: 4,822,278
[45] Date of Patent: Apr. 18, 1989

[54] DENTAL VENEER INSTRUMENT

[75] Inventors: Richard A. Oliva, Los Angeles; Leland M. Perkins, Thousand Oaks; Charles W. Westrick, Huntington Park, all of Calif.

[73] Assignee: The Wilkinson Dental Manufacturing Company, Inc., Westlake Village, Calif.

[21] Appl. No.: 109,995

[22] Filed: Oct. 16, 1987

[51] Int. Cl.$^4$ .............................................. A61C 17/04
[52] U.S. Cl. ........................................ 433/91; 433/50; 433/95; 433/77; 433/141
[58] Field of Search ........................ 433/91, 92, 93, 94, 433/95, 96, 49, 50, 29, 40, 141, 77, 79

[56] References Cited

U.S. PATENT DOCUMENTS

| | | | |
|---|---|---|---|
| 2,979,056 | 4/1961 | Wiseman | 433/92 |
| 3,208,145 | 9/1965 | Turner | 433/95 |
| 3,516,160 | 6/1970 | Leffler | 433/95 |
| 3,721,006 | 3/1973 | Malmin | 433/141 |
| 4,074,435 | 2/1978 | Orsing | 433/96 |
| 4,204,328 | 5/1980 | Kutner | 433/29 |
| 4,353,694 | 10/1982 | Pelerin | 433/77 |
| 4,610,664 | 9/1986 | Harle | 433/95 |

FOREIGN PATENT DOCUMENTS

| | | | |
|---|---|---|---|
| 3204605 | 8/1983 | Fed. Rep. of Germany | 433/91 |
| 2144636 | 3/1985 | United Kingdom | 433/91 |

Primary Examiner—John J. Wilson
Attorney, Agent, or Firm—Kelly, Bauersfeld & Lowry

[57] ABSTRACT

A dental instrument is provided for use in facilitated placement and fixation of dental veneers of fragile porcelain-based material or the like designed for bonding onto patient teeth. The instrument includes a lightweight handpiece adapted for coupling to a vacuum source, in combination with a disposable transparent tip designed to engage and conform with surface contours of a dental veneer for vacuum-holding of the veneer during manipulation preparatory to fixation. A valve port on the handpiece can be opened or closed with a fingertip or with a movable valve member to facilitate controlled pick-up and release of the dental veneer. The transparent tip enhances dentist vision during veneer placement and further permits passage of radiation for improved curing of a light curable bonding agent conventionally used for veneer fixation. A multipurpose vacuum source adapter and alternative instrument geometries are also disclosed.

27 Claims, 4 Drawing Sheets

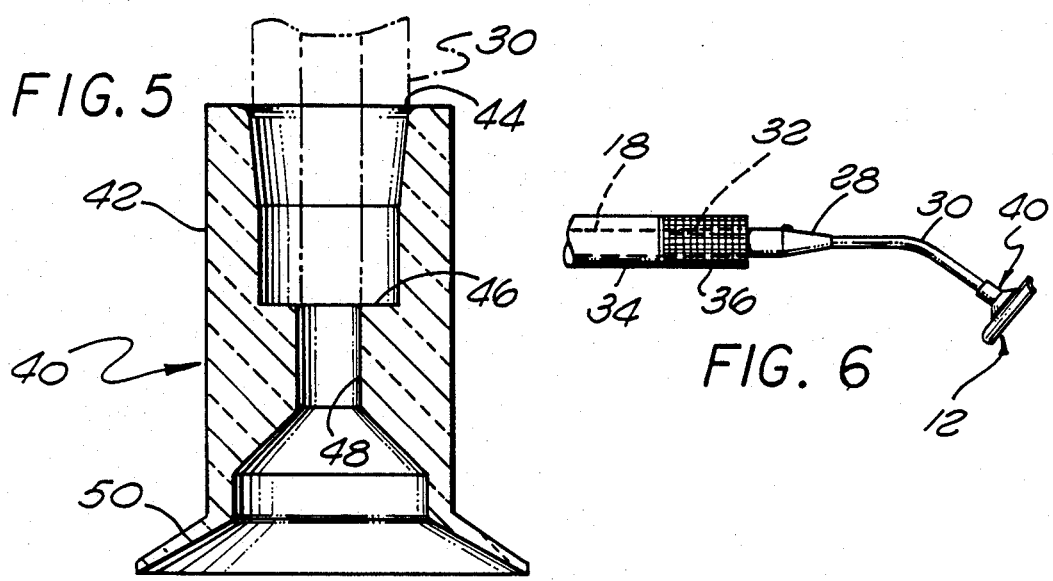
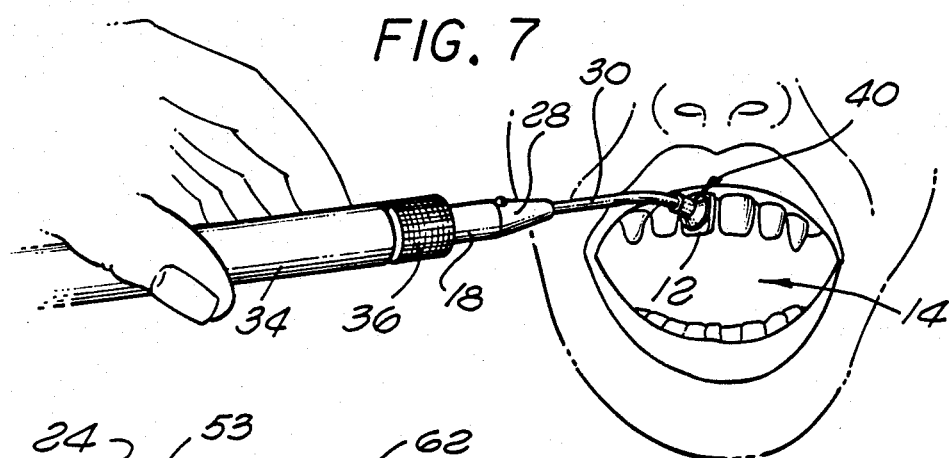
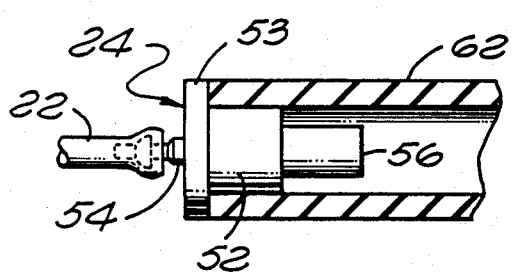
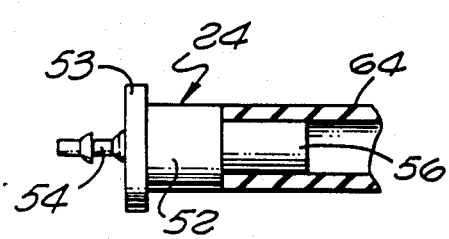
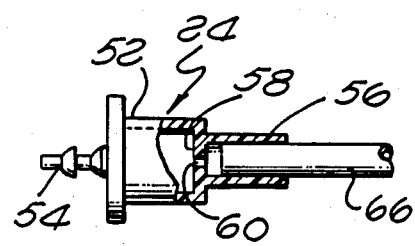

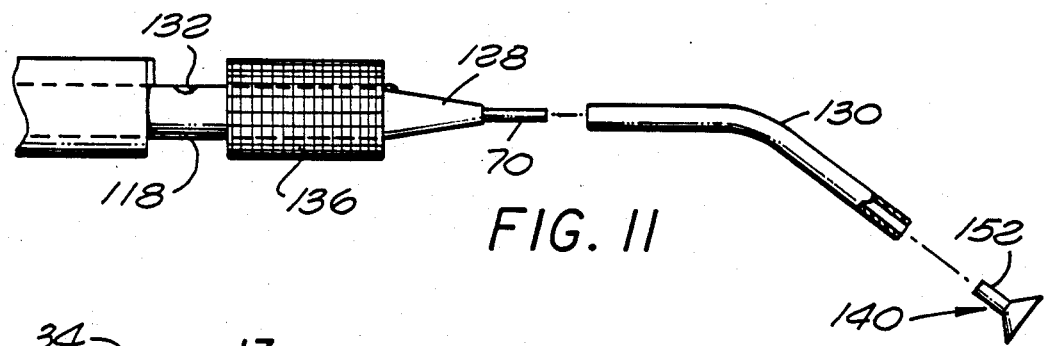
FIG. 11
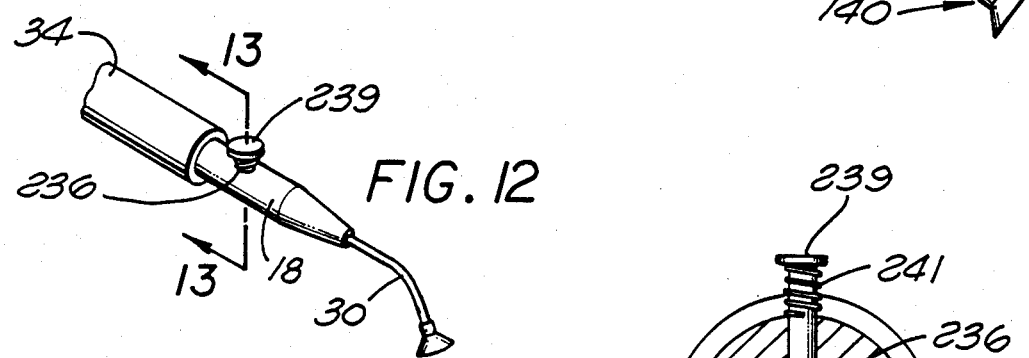
FIG. 12
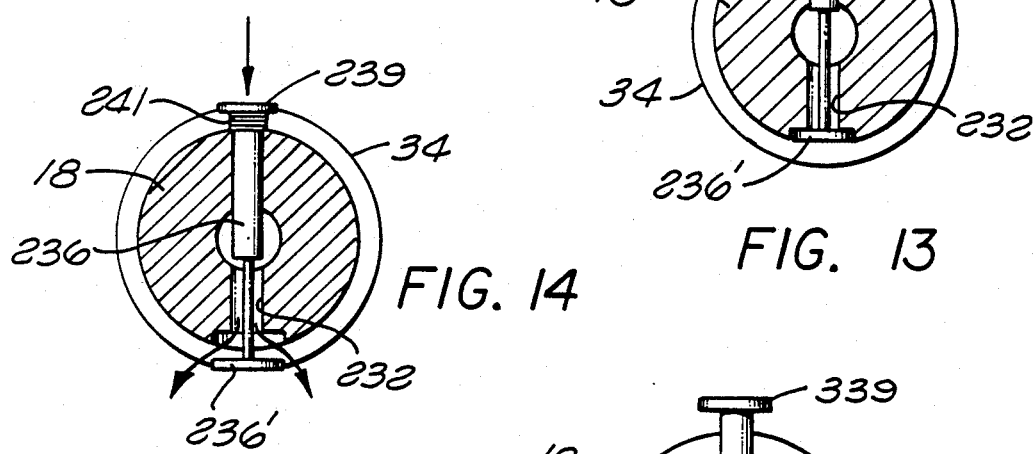
FIG. 13
FIG. 14
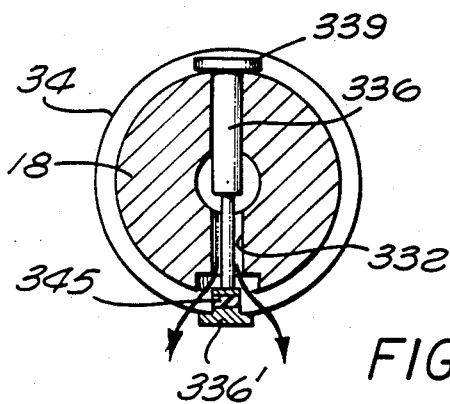
FIG. 16
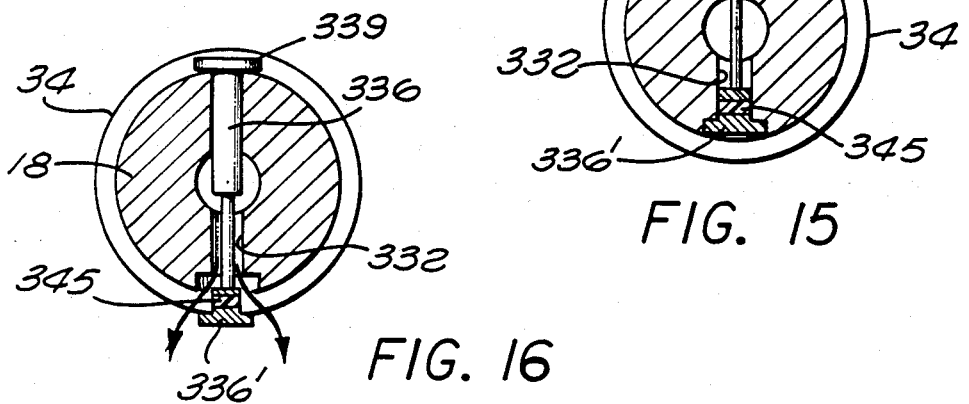
FIG. 15

DENTAL VENEER INSTRUMENT

BACKGROUND OF THE INVENTION

This invention relates generally to dental instruments for use in facilitated handling of dental prostheses. More particularly, this invention relates to a dental instrument designed for improved handling of fragile dental veneers to permit accurate and reliable veneer fixation in a time-efficient manner.

In recent years, the use of dental veneers has become popular as a cosmetic and/or therapeutic dental restoration. Such dental veneers commonly comprise a thin-walled, generally shieldlike cap member having an external geometry with a color typically selected to match adjacent natural or veneered teeth in the patient's mouth. The thin-walled veneer has an interior convex surface prepared by acid etching or the like for secure bonding onto a patient tooth, the surface of which is similarly prepared, for example, by acid etching. A bonding agent is applied to the veneer-tooth interface to securely hold the veneer in place, whereupon the underlying patient tooth structurally supports the fragile veneer to provide a rugged yet cosmetically attractive restoration. While a variety of veneer materials are known, porcelain materials are used most commonly due to their biological compatibility with the oral environment, color stability, and resistance to abrasion.

Despite the popularity of dental veneers, fitting and fixation of a dental veneer within the mouth of a patient tends to be a difficult and time-consuming procedure. More specifically, the dental veneer must be custom prepared in advance to have an interior surface shaped to match the exterior surface of the prepared patient tooth. To this end, a dental veneer is trial fitted by the dentist onto the patient tooth before application of the bonding agent to assure proper fit, color, and form. However, during this trial fit procedure, the prepared patient tooth must be carefully isolated from the remainder of the patient's mouth to prevent contact with saliva or other contaminants which would disrupt the veneer-tooth bonding surface. Such isolation is normally carried out by careful prepreparation of the site including liberal use of rubber dams, cotton rolls, etc. Moreover, the dental veneer is small and very thin in size and thus is extremely fragile prior to fixation. The veneer must therefore be handled carefully during L trial fitting to prevent contamination of its concave acid etched surface. In practice, isolation of the installation site is normally the responsibility of a dental assistant, while the dentist normally concentrates on handling and fitting of the veneer, primarily handling the veneer with the index finger and thumb.

After trial fitting, the dental veneer is removed from the patient's mouth and the bonding agent is applied typically to the interior concave surface of the veneer. The dental veneer is then seated in place upon the prepared patient tooth. A light curable bonding agent such as a resin responsive to selected visible light spectra is popularly used, since it permits final fitting adjustments by the dentist without concern for premature curing of the bonding agent. When a final fit is achieved, the dentist applies a source of the selected light spectra to the veneer to cure the bonding agent and thereby permanently fixate the veneer to the patient's tooth. In practice, this curing step normally requires several applications of the visible light spectra due to the shadowing effects of the dentist's fingers holding the veneer in place.

The foregoing procedure for dental veneer positioning and fixation unfortunately tends to be difficult, tedious, and time consuming. The dental veneer is small and fragile and can be permanently damaged if dropped. The small size of the veneer makes it difficult for the dentist to obtain a clear view during trial or final fitting. Since existing dental instruments are not designed for easy handling of fragile dental veneers, the dentist must hold the veneer in place by fingertip pressure or the like during fitting, color verification, and curing of the bonding agent, but this effectively blocks a portion of the veneer from the dentist's view in addition to delaying the desired rapid cure of the bonding agent. Current use of surgical gloves by dentists and assistants to avoid personal contact with patient body fluids results in significant compounding of these problems. Indeed, while most dentists agree that wearing of gloves is essential to avoid contact with patient body fluids, many dentists nevertheless do not wear gloves during fitting and handling of veneers thereby exposing themselves to patient body fluids.

There exists, therefore, a significant need for improvements in the handling and installation of fragile dental veneers, to permit rapid and accurate veneer fitting and fixation while improving the visibility of the veneer and the installation site throughout an installation procedure. The present related advantages.

SUMMARY OF THE INVENTION

In accordance with the invention, a dental veneer instrument is provided for use in handling a dental veneer of fragile porcelain or the like during implantation into the mouth of a patient. The instrument includes a lightweight handpiece coupled to a vacuum source, and a transparent tip adapted for secure vacuum-holding of the veneer. The transparent tip facilitates manipulation of the veneer during trial fitting and subsequent fixation by greatly enhancing the dentist's view of the work area, and further permits passage of light applied to cure a light curable bonding agent.

In the preferred form, the handpiece has a generally tubular construction formed from a sterilizable material to permit reuse. A rear end of the handpiece is adapted for connection to a lightweight and flexible tubing, whereas the front end terminates in an angularly set probe of reduced diametric size. A valve port is formed in the handpiece near the probe and can be opened or closed manually or, in the alternative, with a valve member mounted on the handpiece for movement between positions respectively opening and closing the valve port. One preferred valve member construction comprises a valve sleeve movable back and forth on the handpiece to open or close the valve port. An elongated cylindrical grip of elastomer material may also be provided about the handpiece for improved manipulative capability.

The transparent tip is formed from a selected and substantially transparent flexible elastomer material having a countersunk upstream end for slide-fit reception of the robe partially into the tip. A downstream end of the tip flares outwardly to define a somewhat cup-shaped base having sufficient flexibility to conform substantially to exterior contours of a dental veneer. A dental veneer can be picked up by closing the valve port on the handpiece manually or by operation of the valve member and then moving the tip base against the veneer such that the veneer is vacuum-supported by the tip.

The vacuum tubing is conveniently connected to a multipurpose vacuum source adapter designed for easy connection to any of a variety of vacuum sources typically available in a dental office. More particularly, the adapter includes an enlarged cylindrical body sized for sliding fit reception into a high volume aspirator tube which is coupled in turn to a suitable vacuum pump. The adapter further includes a smaller diameter barrel sized for slide-fit into a standard sized fitting of a conventional saliva !, aspirator unit. Still further, the adapter barrel defines an inner bore for slide-fit reception of tubing connected in turn to a small portable vacuum pump.

In use, the handpiece and probe of the dental veneer instrument are designed for resterilization for reuse, with the transparent tip and grip being disposable. In one alternative form, the probe may also comprise a disposable component constructed, for example, from a suitable plastic or the like. In other embodiments, alternate valve members such as spring-loaded, friction fit, or quarter-turn valve units can be used, each of which is designed with a set position closing the handpiece valve port. In another alternative embodiment, a nonvalved handpiece can be provided with an integrated probe and tip designed to support a dental veneer during advance preparation steps, such as supporting the veneer within an acid bath to etch selected surfaces thereof.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 5 is an enlarged vertical sectional view showing construction details of a disposable tip for use with the instrument;

FIG. 6 is a fragmented side elevational view similar to a portion of FIG. 2 and illustrating use of the instrument for supporting a dental veneer;

FIG. 7 is a fragmented perspective view similar to FIG. 1 but illustrating use of the instrument to hold a dental veneer during fixation thereof;

FIG. 8 is an enlarged fragmented vertical sectional view showing one construction for coupling the instrument to a vacuum source;

FIG. 9 is an enlarged fragmented sectional view similar to FIG. 8 but depicting an alternative coupling to a vacuum source;

FIG. 10 is an enlarged fragmented sectional view similar to FIG. 8 but showing still another alternative coupling to a vacuum source;

FIG. 11 is an enlarged fragmented side elevation view similar to a portion of FIG. 2 but illustrating an alternative preferred form of the invention;

FIG. 12 is a fragmented perspective view depicting another alternative preferred form of the invention, and showing a spring-loaded valve member for controlling instrument operation;

FIG. 13 is an enlarged vertical sectional view taken generally on the line 13—13 of FIG. 12, and showing the spring-loaded valve member in a normal closed position;

FIG. 14 is a sectional view similar to FIG. 13 but illustrating the spring-loaded valve member depressed to an open position;

FIG. 15 is a vertical sectional view somewhat similar to FIG. 13 but depicting a friction fit valve member in a normally closed position;

FIG. 16 is a vertical sectional view similar to FIG. 15 and showing the friction fit valve member depressed to an open position;

DETAILED DESCRIPTION OF THE PREFERRED EMBODIMENTS

Figure 1:
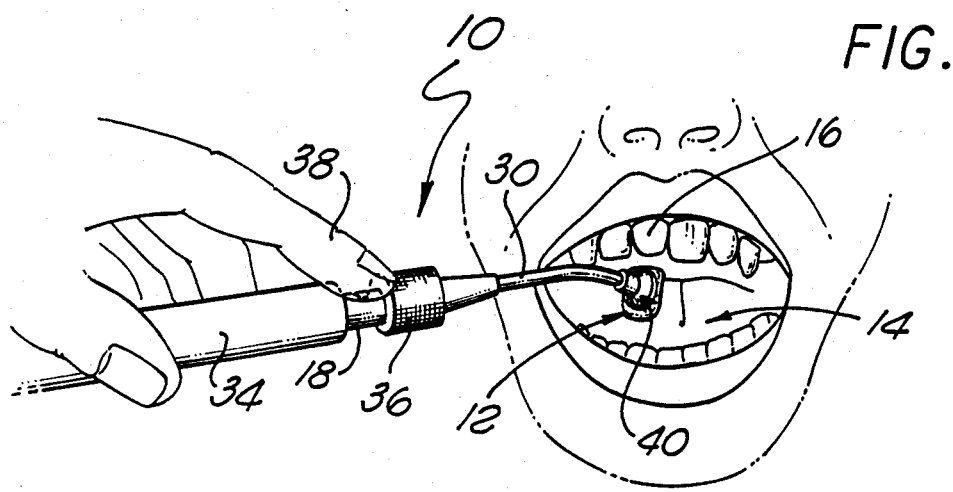
FIG. 1 is a fragmented perspective view illustrating use of a dental veneer instrument embodying the novel features of the invention.

As shown in the exemplary drawings, an improved dental veneer instrument referred to generally by the reference numeral 10 is provided for handling a dental veneer 12 during implantation of the veneer 12 into the mouth 14 of a patient. The instrument 10 is designed to pick up and permit manipulation of the dental veneer 12 in a safe and reliable manner, wherein such handling of the veneer is accompanied by significantly improved visibility of the work area within the patient's mouth. Accordingly, the instrument 10 permits faster and more accurate veneer implantation.

The dental veneer 12 is commonly used in modern dentistry as a cosmetic and/or therapeutic dental restoration or prosthesis. The dental veneer 12 commonly comprises a thin shield-like cap or shield member of a fragile porcelain material or the like typically having a thickness of about 0.3–0.5 mm, wherein the cap member has an exterior or outboard surface and color designed to simulate a natural tooth. The interior or inboard surface of the veneer cap member is normally concave and is prepared by acid etching or the like to create a specific textural surface adapted to bond or cement securely onto a similarly prepared surface of a patient tooth 16, as viewed in FIG. 1. A bonding agent is applied to the veneer-tooth interface to securely mount the veneer in place, with light curable resins being widely used since they permit a degree of positional adjustment of the veneer to a final fit before application of curing radiation. More specifically, a bonding agent curable in response to a selected visible light spectra is commonly used to allow the veneer to be properly positioned by the dentist, at which time a light source probe (not shown) is placed proximally to the veneer for rapid curing of the bonding agent.

The dental veneer instrument 10 of the present invention is designed to pick up and handle a fragile dental veneer 12 without concern for dropping the veneer, wherein such dropping could contaminate the concave interior etched surface or otherwise cause the veneer to crack or break. The instrument 10 permits the veneer 12 to be handled easily for accurate positioning during an initial trial fit within the patient's mouth 14 to insure correct shape, color, marginal fit, etc., and further during final fit including the bonding agent. The instrument 10 beneficially reduces the need for direct fingertip handling of the veneer 12 to correspondingly enhance the dentist's visibility of the working area within the patient's mouth, thereby permitting a faster and more accurate implantation procedure. Moreover, the instrument is designed to support the veneer during curing of the bonding agent, substantially without blocking the curing radiation applied to the veneer, thereby achieving faster and improved curing of the bonding agent. Throughout this implantation procedure, the improved handling of the veneer 12 arising by use of the instrument 10 permits the dentist and a dental assistant to direct more attention to maintaining the work area free of saliva and other contaminants.

Figure 2:
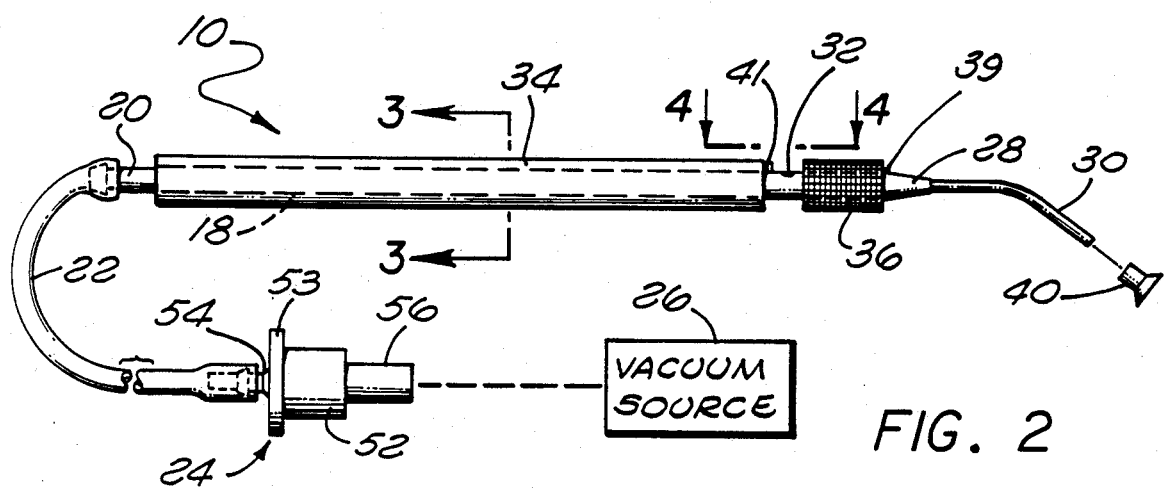
FIG. 2 is a fragmented and partially exploded side elevational view of the dental veneer instrument.
Figure 3:
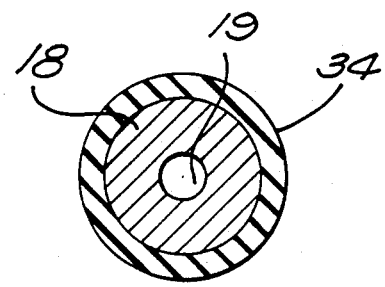
FIG. 3 is an enlarged transverse sectional view taken generally on the line 3—3 of FIG. 2.

As shown generally in FIGS. 1-3, the improved dental veneer instrument 10 of the present invention comprises an elongated handpiece 18 of tubular construction defining an internal flow passage 19. In the preferred form, this handpiece 18 is formed from a sterilizable and thus reusable material such as stainless steel or the like which can be autoclaved. The handpiece 18 has a lightweight overall size and shape designed for precision handling and use during dental procedures. A fitting 20 at the rear end of the handpiece permits connection to an elongated and flexible length of tubing 22 for connection in turn through an adapter 24 to a suitable vacuum source 26, as will be described in more detail. At the front end of the handpiece 18, a conical nose 28 projects outwardly and is connected to a smaller diameter hollow probe 30 which projects forwardly a short distance and then turns angularly downwardly through an angle of about 30°-45°.

Figure 4:
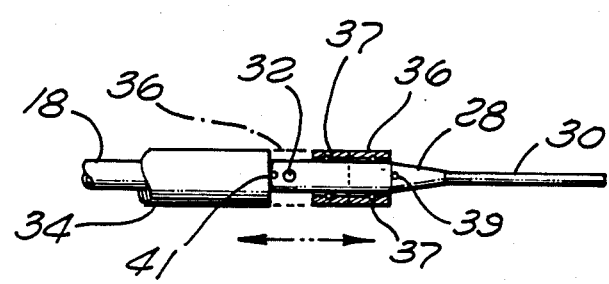
FIG. 4 is a fragmented top plan view taken generally on the line 4—4 of FIG. 2 and depicting portions of the instrument.

A valve port 32 is formed in the handpiece 18 near the front end thereof. As shown in FIGS. 2 and 4, this valve port 32 is positioned slightly in front of an elongated cylindrical grip 34 of an elastomer foam or the like received about a major portion of the handpiece for improved manipulation of the instrument. A valve sleeve 36 is also carried about the handpiece 18 for sliding movement between a first or open position exposing the valve port 32, as shown in solid lines in FIG. 4, and a second or closed position closing the valve port 32, as shown in dotted lines in FIG. 4. The preferred construction of this valve sleeve 36 is a metal sleeve of stainless steel or the like having a knurled or otherwise textured outer surface for improved handling during use. An internal pair of axially spaced O-rings 37 are provided in sealing engagement with the exterior of the handpiece 18 to bridge and close the valve port 32 in a sealed manner. Anterior and posterior stop means such as a forward rivet head 39 and a short rear stop pin 41 can be provided to define the forward and rearward end limits to valve sleeve sliding motion.

In use, the valve port 32 can be allowed to remain open for purposes of breaking the vacuum applied to the handpiece 18 by the vacuum source 26. Alternately, the valve port 32 can be closed to communicate the vacuum to the open forward end of the probe 30 for picking up and handling the dental veneer 12. Such closure of the valve port 32 can be accomplished with the fingertip 38, as viewed in FIG. 1, or by sliding the valve sleeve 36 over the valve port 32, as shown in FIGS. 6 and 7.

In accordance with one primary aspect of the invention, a specialized tip 40 is provided for mounting at the forward or free end of the probe 30 to facilitate handling of the dental veneer 12. More particularly, the tip 40 is formed from a resilient plastic material as a disposable component which can be discarded after each veneer implantation procedure. Moreover, the tip 40 is constructed from a transparent or substantially transparent material to permit viewing by the dentist of the veneer implantation site by observation directly through the tip, while the tip 40 is used to support the veneer within the patient's mouth. This transparency feature further permits the veneer 12 to be held by the tip 40 during radiation curing of a bonding agent, substantially without obstructing the curing radiation.

The preferred construction of the tip 40 is shown in detail in FIG. 5. As shown, the tip 40 has a generally cylindrical body 42 with a countersunk and chamfered upstream end 44 for relatively easy press-fit reception of the probe 30 without requiring the tip to be handled directly during such press-fit mounting. A shoulder 46 within the countersink advantageously provides a stop preventing probe overinsertion into or through a central orifice 48. The orifice 48 opens in turn into the interior of an enlarged chamber which expands within the body 42 and further into a downstream end base 50 of generally outwardly open, cup-shaped geometry. Importantly, the tip walls forming the base 50 are sufficiently thin to provide a relatively high degree of flexibility to conform with a variety of surface contours as represented, for example, by a range of dental veneers corresponding with different types and sizes of patient teeth. This flexibility in combination with the rearwardly spaced position of the probe, permits limited displacement of a dental veneer in virtually all directions while supported by the tip 40, without significant risk of dropping the veneer.

When installed onto the probe 30, the tip 40 can be placed against a dental veneer 12 while closing the handpiece valve port 32. Such valve port closure, of course, may be accomplished manually or with the movable valve member. This applies the vacuum to the tip to correspondingly pick up the veneer by vacuum action. Conversely, opening of the valve port 32 breaks the vacuum applied to the tip 40 and thus is effective to release the veneer.

In a typical veneer installation procedure, the dentist can pick up and manipulate the veneer 12, as shown in FIGS. 1 and 7, while maintaining the valve port 32 closed. This permits easy handling of the veneer 12 during initial trial fitting of the veneer within the patient's mouth 14, since the dentist can easily position the veneer 12 with the probe 30 and, if desired, release the veneer by simple opening of the valve port 32. At all times, the transparent tip 40 advantageously permits a clear view of the work site. When the dentist is satisfied with the trial fit, the dentist can remove the veneer from the patient's mouth quickly and easily, and without fear of dropping the veneer. In this regard, it will be understood that most trial fitting procedures will be performed with the valve member 36 closing the valve port 32 since it permits the dentist and an assistant to hand the veneer and instrument back and forth without fear of dropping the veneer.

After the trial fit, the dentist applies the bonding agent to the veneer-tooth interface typically by applying the bonding agent to the interior concave surface of the veneer. The dentist then uses the instrument to reinstall the veneer 12 onto the patient's tooth 16 at the final desired position. When final fit is achieved, the instrument 10 can be used to hold the veneer in place, as viewed in FIG. 7, during application of curing radiation to the bonding agent. During this step, the transparent tip 40 allows radiation passage substantially to all surfaces of the veneer for an improved rapid cure of the bonding agent. When the implantation procedure is completed, the handpiece 18 can be sterilized, with remaining portions including the tip 40 and grip 34 being disposable.

In accordance with further aspects of the invention, the multipurpose vacuum source adapter 24 accommodates convenient connection to different types of vacuum sources available in a modern dental office. More particularly, as viewed in FIGS. 8–10, the adapter 24 includes an enlarged cylindrical body 52 joined at one end to a barbed fitting 54 for reception into the vacuum tubing 22, and an opposite end defined by a generally cylindrical hollow barrel 56 of reduced diameter. An inner wall 58 (FIG. 10) has an orifice 60 therein to regulate the vacuum level applied through the adapter 24 to the instrument 10. The cylindrical body 52 is sized for slide-fit reception into a high volume aspirator tube 62 (FIG. 8) of the type commonly available in a dental office, with a radial flange 53 at one end of the body 52 preventing overinsertion into the aspirator tube. Alternately, as viewed in FIG. 9, the smaller diameter barrel 56 is sized for sliding fit into a flexible tubing 64 of a standardized saliva aspirator unit (not shown). Still further, as shown in FIG. 10, a smaller tube 66 may be pressed into the hollow bore of the barrel 56 for coupling the adapter 24 to a portable vacuum source. In all cases, the tube or tubing components coupled to the upstream end of the adapter 24 are connected in turn to a suitable vacuum pump, with the adapter orifice 60 providing a substantially constant vacuum level applied to the instrument 10.

One alternative form of the dental veneer instrument is shown in FIG. 11, wherein structural components corresponding functionally with the embodiment of FIGS. 1–7 are identified by common reference numerals increased by 100. More particularly, in this alternative embodiment of the invention, the nose or front end of the handpiece 118 is modified to accommodate removable mounting of a probe 130 which can be formed from plastic or the like for disposal with the tip 140 after use. That is, the front or nose end of the cylindrical handpiece 118 defines a tapered conical nose 128 joined to a forwardly projecting hollow mounting tube 70. This mounting tube 70 is sized for sliding fit into a rear end of the probe 130, which extends forwardly therefrom and then turns through an angle of about 30°–45°. The tip 140 is adapted for press-fit mounting at the front end of the probe 130, with a small diameter tip body 152 being shown for sliding reception into the probe front end.

The modified instrument of FIG. 11 is used in the same manner as described previously with respect to FIGS. 1–7 for supporting and holding a dental veneer 1 during an implantation procedure. A valve port 132 on the handpiece 118 can be closed manually or with a sliding valve sleeve 136. At the conclusion of the implantation procedure, the handpiece 118 is stripped of the probe 130, the tip 140, and a grip 134 to permit resterilization prior to reuse. Alternately, in some cases, it may be preferable to replace only the probe 130 and tip 140 before reuse.

Further alternative configurations for the invention are shown by way of example in FIGS. 12–18, wherein alternate valve structures are illustrated for use in selective closure of the handpiece valve port. More particularly, with reference to FIGS. 12–14, a cylindrical handpiece 18 having the forward probe 30 to carry a transparent tip 40 is equipped further with a spring-loaded valve stem 236 adapted to open or close a lower valve port 232. The stem 236 protrudes upwardly from the handpiece and terminates in an enlarged upper button 239. A spring 241 reacts between the handpiece 18 and the underside of the button 239 to urge the stem 236 upwardly in a manner displacing a lower seal disk 236', to a position closing the valve port 232, as viewed in FIG. 13. In this normal set position of the valve stem 236, a dental veneer can be picked up and handled by the instrument, as previously described. When it is desired to release the veneer, fingertip pressure on the upper button 239 depresses the stem 236 in a manner opening the valve port 232, as viewed in FIG. 14.

A different valve structure is shown in FIGS. 15 and 16, wherein a modified valve stem 336 again includes a lower seal disk 336' for normally closing a lower valve port 332 in the handpiece 18. In this version, the stem 336 carries a crosswise extending friction pin 345 having a size to seat with a friction fit into the valve port 332 (FIG. 15) to retain the seal disk 336' in a position closing the valve port. Such valve port closure, of course, communicates the vacuum to the instrument probe and tip (not shown in FIGS. 15 and 16) for handling a dental veneer. When veneer release is desired, downward fingertip pressure on an exposed upper button 339 effectively displaces the seal disk 336' toward a position opening the valve port 332, as viewed in FIG. 16.

Figure 17:
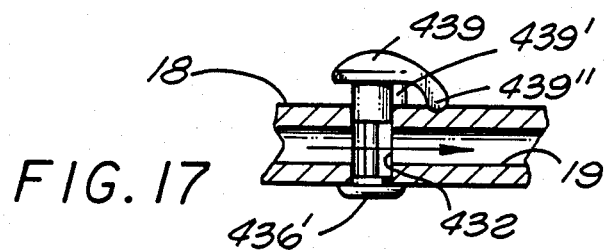
FIG. 17 is a longitudinal vertical sectional view through another alternative form of the dental veneer instrument, and showing a quarter-turn valve member in a closed position.
Figure 18:
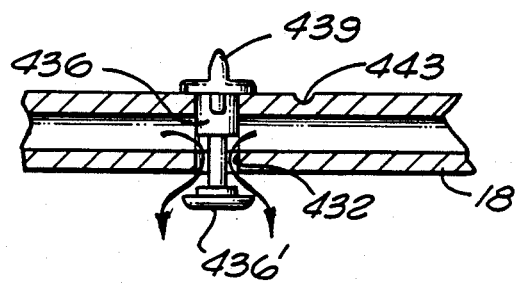
FIG. 18 is a sectional view similar to FIG. 17 but illustrating the quarter-turn valve member in an open position.

FIGS. 17 and 18 show still another valve structure in the form of a quarter-turn device having a valve plug 436 seated within a transversely extending bore 432 which intersects the passage 19 in the handpiece 18. This valve plug 436 includes an upper handle 439 extending perpendicularly to the axis of the valve plug 436, and this handle 439 conveniently includes an underside lug 439' adapted to slide in and out of shallow recessed seats (not shown) on the exterior of the handpiece. A secondary lug 439" may also be provided to seat within a shallow locating dimple 443 on the handpiece.

When the handle 439 is rotated to position with its secondary lug 439" within the handpiece dimple 443, as shown in FIG. 17, the valve plug 436 is axially displaced or elevated within the bore 432 to move a lower seal disk 436' into closing relation with the base. In this position, the vacuum applied to the instrument is communicated to a probe and tip for handling a dental veneer or the like. However, rotation of the handle 439 through a quarter turn in either direction displaces the primary lug 439', into one of the recessed seats, thereby allowing the entire valve plug 436 to drop within the bore 432. This motion moves the seal disk 436' away from the bore 432, such that recesses cut into the valve plug 436 permit venting of the handpiece passage 19 to disrupt the vacuum.

Figure 19:
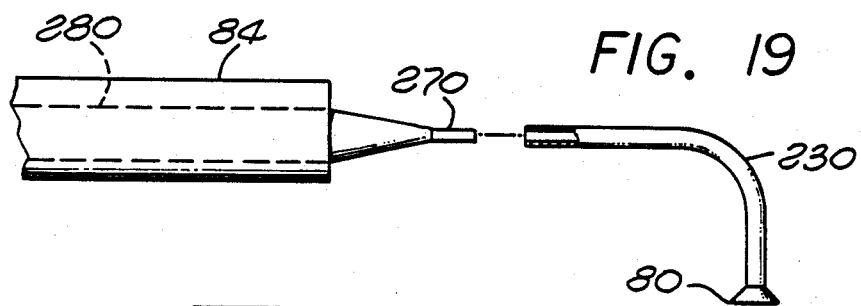
FIG. 19 is an enlarged fragmented side elevational view depicting another alternative embodiment of the invention.
Figure 20:
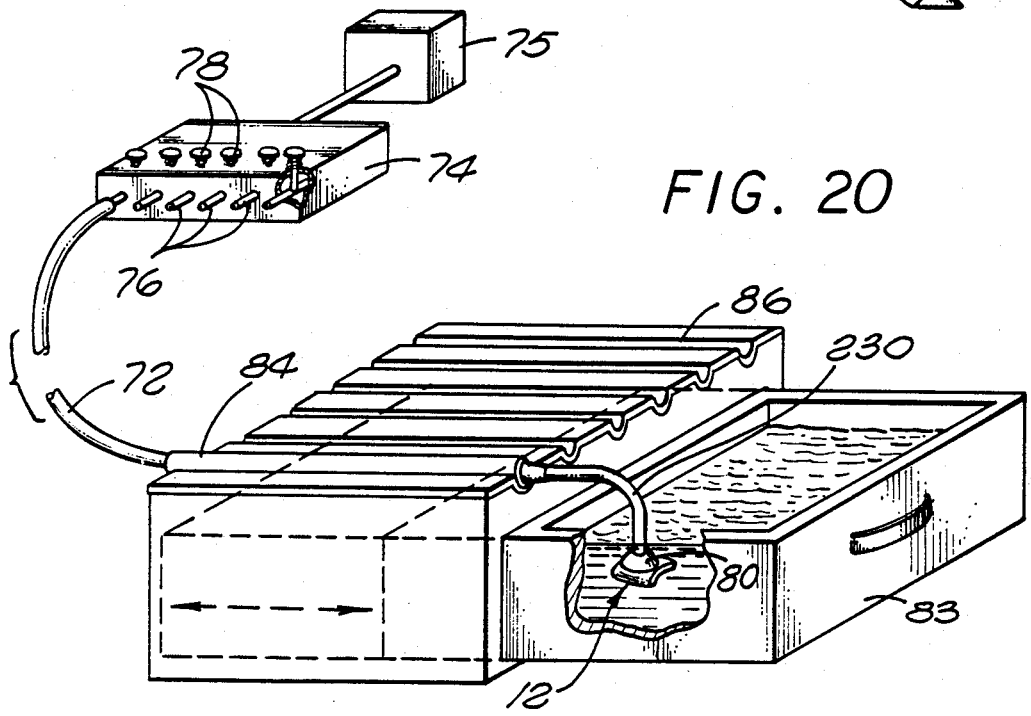
FIG. 20 is a fragmented perspective view illustrating use of the embodiment of FIG. 12 for supporting a dental veneer during an acid etch step.

Still another alternative form of the invention is shown in FIGS. 19 and 20, wherein a further modified instrument is provided for handling dental veneers during prepreparation steps in advance of implantation into the patient's mouth. In this form, a hollow cylindrical handpiece 280 has a rear end adapted for connection to a vacuum tube 72 connected in turn to a vacuum pump 75 via a manifold block 74 preferably having multiple vacuum ports 76 and individual control valves 78 associated with those vacuum ports. A front or nose end of the handpiece 280 terminates in a hollow mounting tube 270 for convenient press-on mounting of a tubular probe 230 of plastic material or the like. This probe 230 is shown with a substantially perpendicular bend intermediate the length thereof and a resilient flared base 80 at its downstream end. This base 80 may be a separate press-on component, as viewed in FIG. 11, or formed integrally with the probe 230, as desired.

In use of the embodiment of FIGS. 19 and 20, a dental veneer 12 has its exterior surface coated with a protective substance such as a wax coating or the like, and its interior concave surface uncoated for exposure to an acid bath 82 for etching the interior surface to achieve an improved bond when implanted. The handpiece 280, which may include a resilient outer grip 84, is placed within a recess on a tray 86 positioned alongside the bath 82, with the veneer 12 supported by the probe 230 and the base 80 submerged within the bath 82 for the duration of the etching step. Appropriate operation of the associated vacuum control 78 is effective to couple or uncouple the veneer to the vacuum pump 75 and thereby permit veneer pick-up and release. In this regard, the control valves 78 conveniently comprise spring-loaded valves designed for normally coupling the respective valve ports 76 to the pumpt 75, and for manual depression to interrupt the vacuum when veneer release, etc. is desired. Moreover, as depicted in FIG. 20, the tray 86 and bath 82 are conveniently provided as an integrated assembly with the tray 86 forming a portion of a housing adapted for slide-in reception of a bath-containing basin 83.

Accordingly, the invention provides an improved instrument for handling of fragile dental veneers and the like in a safe and reliable manner. The preferred form of the invention includes a transparent tip 40 for enhanced viewing of the implantation work area and to avoid obstructing radiation used to cure the applied bonding agent.

A variety of further modifications and improvements to the present invention will be apparent to those skilled in the art. Accordingly, no limitation on the invention is intended by way of the foregoing description and accompanying drawings, except by way of the appended claims.

What is claimed is:

1. A dental instrument for use in supporting and handling a dental veneer or the like, said instrument comprising:
   an elongated handpiece having front and rear ends and defining an internal passage extending therebetween, said rear end being adapted for connection to a vacuum source; and
   a substantially transparent tip mounted generally at said front end of said handpiece, said tip being formed from a resilient elastomer and defining an outwardly opening and generally cup-shaped base for engaging a dental veneer, the interior of said generally cup-shaped base being in communication with said handpiece internal passage whereby the dental veneer is vacuum-supported against said base when said handpiece internal passage is coupled to the vacuum source.

2. The dental instrument of claim 1 wherein said handpiece includes a generally tubular probe projecting from the front end thereof, said probe having a free end with a size for slide-fit mounting with respect to said tip.

3. The dental instrument of claim 2 wherein said tip includes a generally cylindrical body having a countersink in one end thereof for slide-fit reception of said probe free end, said tip body further defining an internal shoulder forming a stop to prevent insertion of said probe free end into the interior of said base, thereby maintaining flexibility of said base substantially independent of said probe, and means defining an orifice communicating between said countersink and said base.

4. The dental instrument of claim 2 wherein said tip includes a generally cylindrical body sized for slide-fit reception into said probe free end.

5. The dental instrument of claim 2 wherein said probe includes a bend generally intermediate the length thereof, said bend having a magnitude in the range of about 30° to about 45°.

6. The dental instrument of claim 2 wherein said probe is removably mounted at said front end of said handpiece and defines an internal path communicating between the interior of said cup-shaped base and said handpiece internal passage.

7. The dental instrument of claim 6 wherein said probe is formed from a plastic material.

8. The dental instrument of claim 1 wherein said handpiece is formed from a resterilizable material.

9. The dental instrument of claim 8 wherein said handpiece is formed from an autoclavable material.

10. The dental instrument of claim 1 further including a resilient grip mounted on said handpiece.

11. The dental instrument of claim 1 further including a valve port formed in said handpiece, said valve port when open interrupting the vacuum within said handpiece internal passage when said internal passage is connected to the vacuum source to interrupt communication of the vacuum to said tip.

12. The dental instrument of claim 11 wherein said valve port is formed generally adjacent said front end of said handpiece.

13. The dental instrument of claim 11 further including a valve member on said handpiece for movement between a first position opening said valve port and a second position closing said valve port.

14. The dental instrument of claim 13 wherein said handpiece has a generally tubular construction, and further wherein said valve member comprises a valve sleeve carried about said handpiece for sliding movement between said first and second positions.

15. The dental instrument of claim 13 wherein said valve member has a normal set position closing said valve port.

16. The dental instrument of claim 15 wherein said valve member comprises a spring-loaded valve member.

17. The dental instrument of claim 15 wherein said valve member comprises a friction fit valve member.

18. The dental instrument of claim 13 wherein said valve member comprises a quarter-turn valve member.

19. The dental instrument of claim 1 further including a length of flexible tubing having one end connected to said handpiece rear end, and a vacuum source adapter having a fitting connected to the other end of said tubing, said adapter having a generally cylindrical body, and a generally cylindrical barrel having a reduced diametric size relative to said body and extending generally coaxially therefrom, said cylindrical body and said barrel being adapted for connection to different vacuum sources.

20. The dental instrument of claim 19 wherein said barrel defines an outer diameter surface and an inner bore for connection to different vacuum sources.

21. A dental instrument for use in supporting and handling a dental veneer or the like, said instrument comprising:

an elongated and generally tubular handpiece having front and rear ends and defining an internal passage extending therebetween, said handpiece further defining a valve port formed therein near said front end;

a hollow tubular probe connected to the front end of said handpiece and extending generally forwardly therefrom, said probe defining an internal path communicating with said handpiece passage and further including a free end presented in a direction generally away from said handpiece;

a valve sleeve on said handpiece for sliding movement between a first position exposing said valve port and a second position substantially covering and sealing said valve port;

means for coupling said rear end of said handpiece to a vacuum source communicating with said handpiece pas and a flexible, substantially transparent outwardly presented and generally cup-shaped tip mounted at said probe free end with the interior of said cup-shaped tip communicating with said probe path, whereby said tip is adapted to conform with exterior surface contours of and to vacuum-support a dental veneer when said valve port is closed.

22. The dental instrument of claim 21 wherein said valve port is positioned for fingertip closure when said valve sleeve is in said first position.

23. The dental instrument of claim 21 wherein said tip includes a cup-shaped base and mounting means, said mounting means being for slidable mounting of said probe free end, and further for defining a stop to prevent insertion of said probe free end into the interior of said cup-shaped base.

24. The dental instrument of claim 21 wherein said tip and said probe are integrally formed, said probe and tip being removably mounted on said handpiece.

25. The dental instrument of claim 21 wherein said probe has an intermediate bend therein at an angle of about 30° to about 45°.

26. The dental instrument of claim 21 further including a resilient cylindrical grip mounted about said handpiece.

27. The dental instrument of claim 21 further including stop means on said handpiece for limiting the range of motion of said valve sleeve.

* * * * *